(12) United States Patent
Yamaguchi et al.

(10) Patent No.: US 12,390,100 B2
(45) Date of Patent: Aug. 19, 2025

(54) MEASURING METHOD FOR MEASURING SENSING CAPABILITY OF EYE OF SUBJECT, AND SETTING METHOD FOR PROGRESSIVE POWER LENS

(71) Applicant: HOYA LENS THAILAND LTD., Pathumthani (TH)

(72) Inventors: Eiichiro Yamaguchi, Tokyo (JP); Toshiaki Sonehara, Tokyo (JP); Ayumu Ito, Tokyo (JP); Nagisa Ishihara, Tokyo (JP)

(73) Assignee: HOYA LENS THAILAND LTD., Pathumthani (TH)

( * ) Notice: Subject to any disclaimer, the term of this patent is extended or adjusted under 35 U.S.C. 154(b) by 916 days.

(21) Appl. No.: 17/599,845

(22) PCT Filed: Mar. 26, 2020

(86) PCT No.: PCT/JP2020/013669
§ 371 (c)(1),
(2) Date: Sep. 29, 2021

(87) PCT Pub. No.: WO2020/203649
PCT Pub. Date: Oct. 8, 2020

(65) Prior Publication Data
US 2022/0160224 A1 May 26, 2022

(30) Foreign Application Priority Data
Mar. 29, 2019 (JP) .................................. 2019-066420

(51) Int. Cl.
*A61B 3/028* (2006.01)
*A61B 3/00* (2006.01)
(Continued)

(52) U.S. Cl.
CPC .............. *A61B 3/028* (2013.01); *A61B 3/005* (2013.01); *A61B 3/0091* (2013.01); *G02C 7/027* (2013.01); *G02C 7/066* (2013.01)

(58) Field of Classification Search
CPC ........ G02C 7/024; G02C 7/025; A61B 3/024; G02B 2027/0178; G02B 27/0093
(Continued)

(56) References Cited

U.S. PATENT DOCUMENTS 5,801,810 A * 9/1998 Roenker ................ A61B 3/024
351/224
6,257,721 B1 * 7/2001 Hayashi ............... G02C 13/003
351/204
(Continued)

FOREIGN PATENT DOCUMENTS

CN 106030384 A 10/2016
GB 2 542 759 A 4/2017
(Continued)

OTHER PUBLICATIONS

Jun. 23, 2020 International Search Report issued in International Patent Application No. PCT/JP2020/013669.
(Continued)

*Primary Examiner* — Zachary W Wilkes
(74) *Attorney, Agent, or Firm* — Oliff PLC

(57) ABSTRACT

A measuring method for measuring sensitivity of eye around certain line of sight includes: showing image of predetermined pattern on a display screen showing in front of eyeball of subject by display device secured to head; showing fixation target focused on by subject, on display screen to make line of sight of subject; showing change region where predetermined pattern image is changed, at anisotropic area around intersection point or fixation target in screen is separated from intersection point and fixation target, inter-
(Continued)

section point wherein subject certain line of sight focuses on fixation target, crosses display screen; showing change region where predetermined image pattern is changed on display screen, wherein change region manner is continuously or intermittently brought close to or away from intersection point or fixation target in display screen; and determining range wherein subject senses change region by bringing it close or away from intersection point or fixation target.

21 Claims, 5 Drawing Sheets

(51) Int. Cl.
    *G02C 7/02*     (2006.01)
    *G02C 7/06*     (2006.01)

(58) Field of Classification Search
    USPC .......................................... 351/224, 237, 246
    See application file for complete search history.

(56) References Cited

U.S. PATENT DOCUMENTS

| | | | | |
|---|---|---|---|---|
| 6,474,817 B1* | 11/2002 | McKinnon | ............. | A61B 3/024 |
| | | | | 351/243 |
| 7,914,148 B2* | 3/2011 | Fisher | ..................... | G06F 30/20 |
| | | | | 351/200 |
| 8,303,113 B2* | 11/2012 | Esser | ..................... | G02C 7/061 |
| | | | | 351/159.75 |
| 8,583,406 B2* | 11/2013 | Shinohara | ............... | G06F 30/20 |
| | | | | 703/2 |
| 8,851,678 B2* | 10/2014 | Pelah | ..................... | A61B 3/024 |
| | | | | 351/224 |
| 9,629,976 B1* | 4/2017 | Acton | ....................... | A61H 5/00 |
| 10,251,543 B2* | 4/2019 | Foster | ..................... | A61B 3/032 |
| 10,582,876 B2* | 3/2020 | Suzuki | ..................... | A61B 3/036 |
| 11,754,856 B2* | 9/2023 | Yoshida | ................. | A61B 3/032 |
| | | | | 351/237 |
| 2015/0286070 A1 | 10/2015 | Aikawa | | |
| 2016/0242670 A1 | 8/2016 | Suzuki et al. | | |
| 2017/0049316 A1 | 2/2017 | Donaldson | | |
| 2017/0209044 A1 | 7/2017 | Ito et al. | | |
| 2017/0351114 A1 | 12/2017 | Calixte et al. | | |
| 2020/0133022 A1* | 4/2020 | Yoshida | ................. | A61B 3/032 |
| 2020/0285074 A1* | 9/2020 | Zimanyi | ................. | G02C 7/061 |

FOREIGN PATENT DOCUMENTS

| | | | |
|---|---|---|---|
| JP | 2002107679 A * | 4/2002 | |
| JP | 4151913 B1 | 9/2008 | |
| JP | 2009-136663 A | 6/2009 | |
| JP | 2013-085709 A | 5/2013 | |
| JP | 2016-022150 A | 2/2016 | |
| WO | 2015/040950 A1 | 3/2015 | |
| WO | 2015/053210 A1 | 4/2015 | |
| WO | 2016/009739 A1 | 1/2016 | |
| WO | 2019/009034 A1 | 1/2019 | |

OTHER PUBLICATIONS

Oct. 10, 2023 Office Action issued in Japanese Patent Application No. 2021-511924.
Mar. 24, 2022 extended Search Report issued in European Patent Application No. 20782447.5.

* cited by examiner

MEASURING METHOD FOR MEASURING SENSING CAPABILITY OF EYE OF SUBJECT, AND SETTING METHOD FOR PROGRESSIVE POWER LENS

FIELD

The present invention relates to a measuring method for measuring sensitivity of an eye around a certain line of sight that is maintained by a subject and also relates to a designing method for designing a progressive power lens by using measurement result of the measuring method.

BACKGROUND

Eyeglass lenses using progressive power lenses are publicly known. The progressive power lens has regions of a distance vision part for distance viewing, a near vision part for near viewing, and an intermediate vision part positioned between the distance vision part and the near vision part, and the progressive power lens changes in refractive power between the distance vision part and the near vision part.

The progressive power lens is designed by determining a spherical power at the distance measurement position, a cylindrical power and an addition power, in accordance with the distance power, astigmatism power, and near power of a person who will purchase eyeglasses (hereinafter simply called a "purchaser").

A progressive power lens is individually designed so as to be suitable for an eye of each purchaser by adjusting a spherical power, a cylindrical power, and an addition power. For a progressive power lens more suitable for an eye of a purchaser, it is preferable to take into consideration sensitivity of an eye around a line of sight that is maintained to be directed to a direction other than forward, in addition to a spherical power, a cylindrical power, and an addition power. The sensitivity of an eye around a line of sight differs for each purchaser.

For example, a method for quantitatively measuring a field of view of a subject is publicly known (Patent literature 1).

This method for measuring a field of view is performed as follows. A face image containing a human face is shown so that a subject will look at it straightly from forward. Then, visual stimuli are generated at multiple positions that have mutually different distances from a target fixation point determined in an area of face in the face image. On the basis of positions where a subject recognized the generated visual stimuli, a field of view of the subject is measured. The visual stimuli are generated in an area of the hair of head and in an area outside the head, including the face and the hair, in the face image.

CITATION LIST

Patent Literature

Patent literature 1: Japanese Unexamined Patent Application Laid-Open No. 2013-085709

BRIEF SUMMARY

Technical Problem

In the above method, a field of view of a subject is measured only in the state in which the subject looks forward straightly. Thus, the above method fails to disclose a technique for measuring sensitivity of an eye around a line of sight that is maintained in a certain direction.

In particular, blurring of an image easily occurs in a side area laterally separated from a main fixation axis, in the intermediate vision part or the near vision part in a progressive power lens. Sensitivity to this blurring of an image varies depending on the person. That is, a sensible range in which a blur of an image extends in a side area from the intermediate vision part to the near vision part differs between individuals. For this reason, it is preferable to measure sensitivity of an eye around a certain line of sight that is maintained, in terms of providing a progressive power lens more suitable for a purchaser of an eyeglass lens.

In view of this, an object of the present invention is to provide a measuring method for measuring sensitivity of an eye around a certain line of sight that is maintained by a subject and to provide a designing method for designing a progressive power lens by using measurement result of the measuring method.

Solution to Problem

An embodiment of the present disclosure is a measuring method for measuring sensitivity of an eye around a certain line of sight that is maintained by a subject. The measuring method includes:

showing an image of a predetermined pattern on a display screen, the display screen being shown in front of an eyeball of the subject by a display device that is secured to a head of the subject;

showing a fixation target to be focused on by the subject, on the display screen, in order to make a line of sight of the subject be the certain line of sight;

showing a change region where the image of the predetermined pattern is changed, at an anisotropic area around an intersection point or the fixation target in the display screen, the anisotropic area being separated from the intersection point and the fixation target, the intersection point being where the certain line of sight of the subject focusing on the fixation target, crosses the display screen;

showing the change region where the image of the predetermined pattern is changed, on the display screen, in such a manner that the change region is continuously or intermittently brought close to or away from the intersection point or the fixation target in the display screen; and determining a range in which the subject can sense the change region, in response to the change region shown by bringing the change region close to or away from the intersection point or the fixation target, whereby the sensitivity of the eye is measured.

Preferably, the change region may be at least one continuous region that continuously extends from a side edge of the display screen relative to the intersection point, toward the intersection point or the fixation target.

Preferably, the change region may be at least one continuous region that continuously extends from an upper edge or a lower edge of the display screen relative to the intersection point, toward the intersection point or the fixation target.

Preferably, the change region may be formed on at least one of right and left sides bounded by a vertical line that is parallel to an up-down direction of the display screen while passing the intersection point, and the change region does not cross the vertical line.

Preferably, the fixation target may be a region having predetermined dimensions,
 the change region is provided so as to surround the region of the fixation target and has a largest degree of change of the image of the pattern in the display screen, and
 the change region is surrounded by a region that has a small degree of the change compared with the degree of the change in the change region or does not have the change.

Preferably, the change region may include a blurred image of the pattern.

Preferably, the measuring method may include comprising showing the pattern by changing a degree of blurring of the image of the pattern in the change region in a predetermined range, at the time of showing the change region on the display screen.

Preferably, the sensitivity of the eye may include information of a sensible distance of the change region from the intersection point in the condition in which the change region can be sensed by the subject and is most separated from the intersection point.

Preferably, the sensible distance may be determined in accordance with the degree of blurring, and
 the sensitivity of the eye includes information of a set of the degree of blurring and the sensible distance corresponding to the degree of blurring.

Preferably, the certain line of sight may be in a direction different from a direction of a line of sight of the subject looking forward straightly.

Preferably, the certain line of sight may be directed downward relative to the line of sight of the subject looking forward straightly.

Preferably, the image of the pattern shown on the display screen, in a region other than the change region, may have a constant degree of the change irrespective of the position in the display screen.

An embodiment of the present disclosure is a designing method for a progressive power lens suitable for an eye of a subject, the progressive power lens having regions of a distance vision part for distance viewing, a near vision part for near viewing, and an intermediate vision part positioned between the distance vision part and the near vision part, the progressive power lens changing in refractive power between the distance vision part and the near vision part. The designing method includes:
 showing an image of a predetermined pattern on a display screen, the display screen being shown in front of an eyeball of the subject by a display device that is secured to a head of the subject;
 showing a fixation target to be focused on by the subject, on the display screen, in order to make a line of sight of the subject be a line of sight directed downward relative to a line of sight of the subject looking forward straightly;
 showing a change region where the image of the predetermined pattern is changed, at an anisotropic area around an intersection point or the fixation target in the display screen, the anisotropic area being separated from the intersection point and the fixation target, the intersection point being where the line of sight directed downward of the subject focusing on the fixation target, crosses the display screen;
 showing the change region, where the image of the predetermined pattern is changed, on the display screen, in such a manner that the change region is continuously or intermittently brought close to or away from the intersection point or the fixation target in the display screen;
 determining a range in which the subject can sense the change region, in response to the change region shown by bringing the change region close to or away from the intersection point or the fixation target, whereby the sensitivity of the eye is measured; and
 designing a refractive power distribution suitable for the subject on a basis of information of the measured sensitivity of the eye.

Advantageous Effects

The measuring method enables measuring sensitivity of an eye around a certain line of sight that is maintained by a subject. As a result, it is possible to design a progressive power lens suitable for sensitivity of an eye that differs depending on the purchaser of an eyeglass lens.

DETAILED DESCRIPTION

The following describes a measuring method and a designing method for a progressive power lens according to one embodiment of the present invention, based on the attached drawings.

Figure 1:
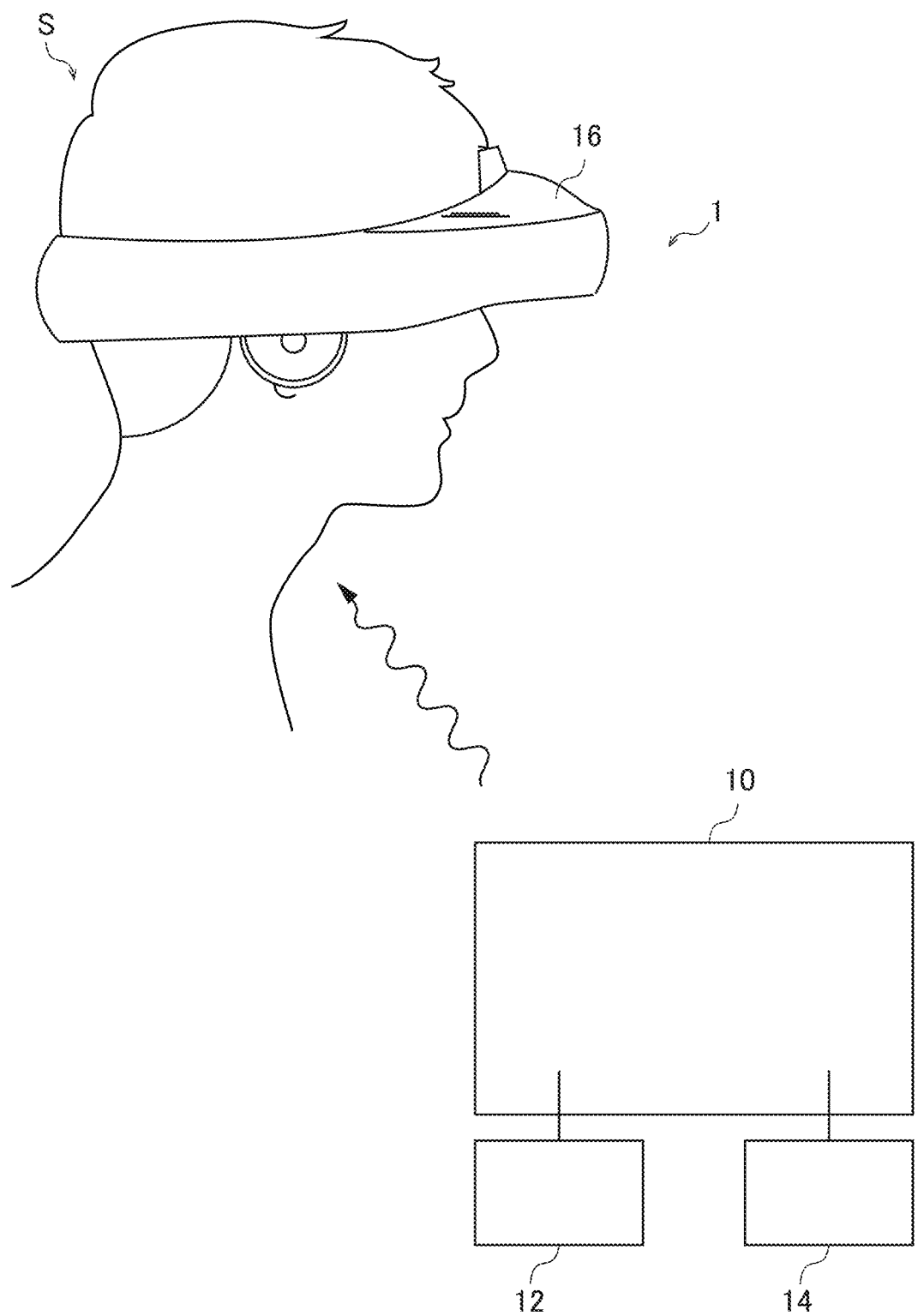
FIG. 1 shows a schematic configuration of a measurement system that implements a measuring method for measuring sensitivity of an eye of a subject according to one embodiment.

FIG. 1 shows a schematic configuration of a measurement system 1 that implements a measuring method for measuring sensitivity of an eye of a subject according to an embodiment.

The sensitivity of an eye, which is measured by the measurement system 1, is an ability of an eye relating to whether a subject can recognize change of an image of a pattern shown around a certain line of sight, while focusing on a certain part of the pattern and maintaining the certain line of sight. The image of the pattern is predetermined and is shown on a display screen. This sensitivity is different from sensibility of a subject that is examined in terms of a degree of endurance with psychological pain. The psychological pain is caused by change of a pattern, for example, a blurred pattern, in a state in which the change of the pattern is recognized.

The measurement system 1 primarily includes a computer 10 and a head-mounted display 16.

The head-mounted display 16 is a display device that shows a display screen in front of an eyeball of a subject "S", in a state of being secured to the head of the subject "S". FIG. 1 shows an example of using the head-mounted display 16 as a display device, but any display device can be used on the condition that it shows a display screen in front of an eyeball of the subject "S" in a state of being secured to the head of the subject "S".

The computer 10 is connected to an input operation system 12 including a mouse, a keyboard, an input mechanism that allows input by operating a button, or the like, and the computer 10 is also connected to a monitor 14. The monitor 14 displays information such as a result of measuring sensitivity of an eyeball, and a pattern and a change region of the pattern that are shown on the display screen of the head-mounted display 16 during measurement, which will be described later. Moreover, a measurement condition setting screen is also displayed to allow setting details of a procedure of the measuring method for measuring sensitivity of an eyeball.

The computer 10 includes a memory, which is not shown in the drawing, and measurement software for measuring sensitivity of an eye is recorded in the memory. The computer 10 reads and drives this measurement software and thereby makes the head-mounted display 16 show display information on the display screen, as described below.

Specifically, the head-mounted display 16 shows an image of a predetermined pattern on the display screen in accordance with an instruction from the computer 10. Moreover, in order to make a line of sight of a subject "S" be a certain line of sight, a fixation target to be focused on by the subject "S" is shown on the display screen. Herein, the pattern is preferably a series of unit element shapes that are continuous vertically and laterally. Examples of the pattern include a lattice pattern and a checkered pattern in which black and white rectangular regions are arranged alternately with each other.

The fixation target occupies a certain area defined by, for example, a rectangular frame, a circular frame, or a circle.

Figure 2:
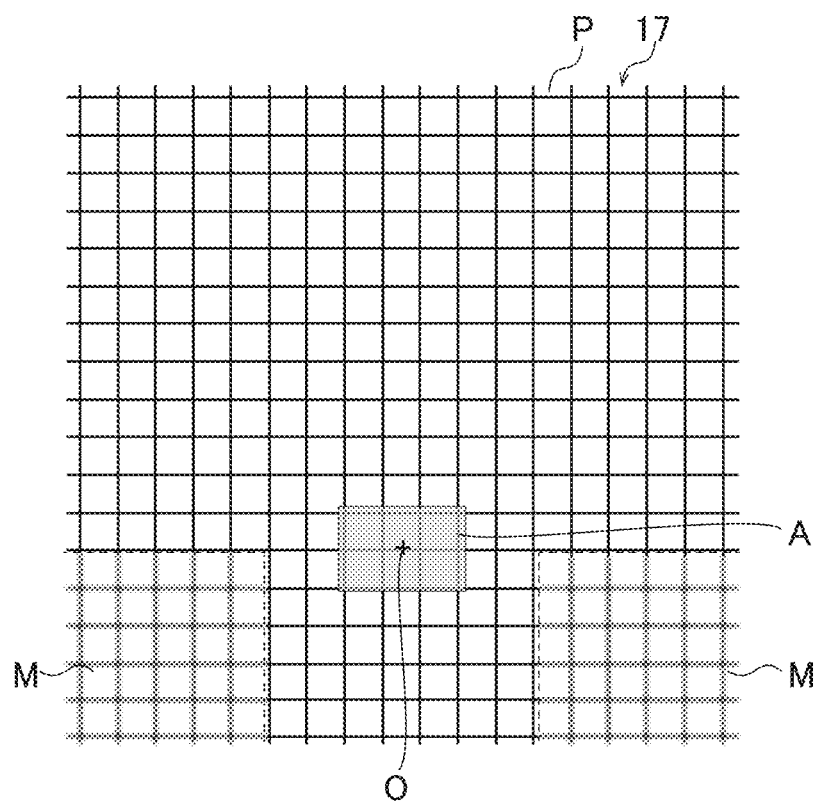
FIG. 2 shows an example of a pattern that is shown on a display screen used in one embodiment.

FIG. 2 shows an example of a pattern "P" that is shown on a display screen 17. The pattern "P" is a lattice pattern, and rectangular lattices are arranged on the display screen 17. It is preferable that approximately 10 to 30 lattices be arranged vertically and laterally on the display screen 17, in terms of measuring sensitivity for a change region. In addition, the rectangular shapes of the arranged lattices are preferably square.

The subject "S" aims the line of sight at a fixation target "A" in accordance with an instruction. In the example shown in FIG. 2, the fixation target "A" is a region enclosed by a rectangular frame.

Moreover, the head-mounted display 16 shows a change region where the image of the pattern "P" is changed, at an anisotropic area around an intersection point "O" or the fixation target "A" in the display screen 17. The anisotropic area is separated from the intersection point "0" and the fixation target "A". The intersection point "O" is where a certain line of sight of the subject "S" focusing on the fixation target "A" crosses the display screen 17. The intersection point "O", which is a point where a line of sight of the subject "S" focusing on the fixation target "A" crosses the display screen 17, corresponds to an approximately center point in the region of the fixation target "A".

FIG. 2 shows a change region "M" where an image of lattice lines is blurred. The change region "M" may have a deformed shape in which an original shape, such as a rectangular shape of a lattice pattern, is deformed, instead of a blur of an image. Alternatively, the change region may be a region where a difference in brightness between the lattice lines and a background area is varied from that in an area other than the change region. The anisotropic region means a region other than an isotropic region that is defined by a circular shape centering at the intersection point "O" or the fixation target "A".

In view of this, the anisotropic region also includes a disk-shaped area having a circular hole at its center and having a cut part.

Furthermore, the head-mounted display 16 shows a change region where the image of the displayed pattern is changed, on the display screen 17, in such a manner that the change region is continuously or intermittently brought close to or away from the intersection point "O" or the fixation target "A" in the display screen 17. Continuously bringing the change region closer or farther away means bringing the change region closer or farther away at a predetermined rate. Intermittently bringing the change region closer or farther away means bringing the change region closer or farther away at a constant time interval. In this case, a change region having a certain area or a certain shape may be brought close to or away from the intersection point "O" or the fixation target "A". Alternatively, a change region, which extends from an edge of the display screen 17, may approach in such a manner as to be enlarged toward the intersection point "O" or the fixation target "A", or may be separated in such a manner as to be retracted from the intersection point "O" or the fixation target "A" toward the edge of the display screen 17.

Figure 3A:
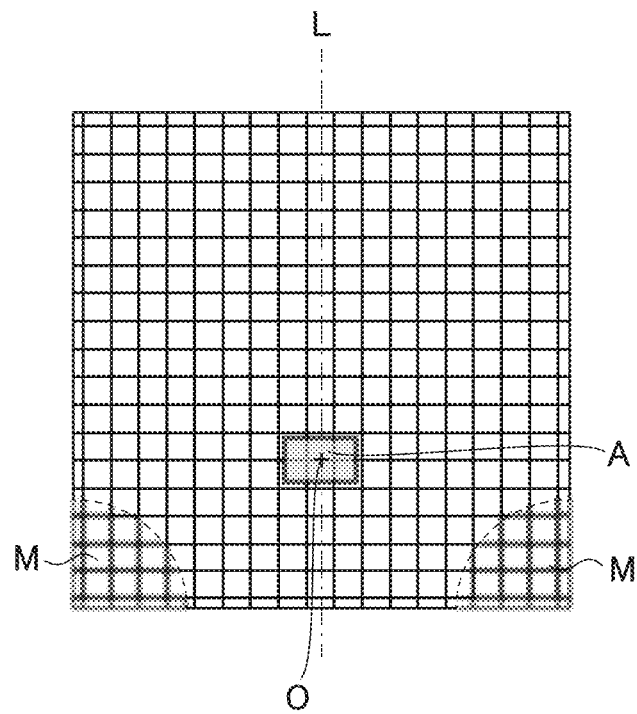
FIGS. 3A and 3B are explanatory drawings of examples of change regions used in one embodiment.
Figure 3B:
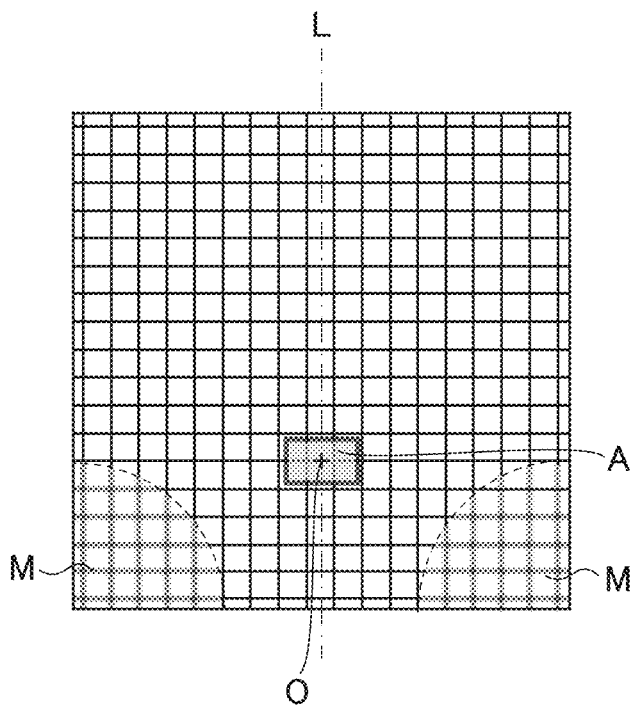

FIGS. 3A and 3B are explanatory drawings of examples of change regions. In the example shown in FIG. 3A, the change region "M" extends from an edge of the display screen 17 and has a small area. In the example shown in FIG. 3B, the change region "M" extends from an edge of the display screen 17 and has an area larger than that of the change region "M" shown in FIG. 3A, whereby the change region "M" comes close to the intersection point "O" or the fixation target "A".

The head-mounted display 16 shows the change region "M" in such a manner that the change region "M" is continuously or intermittently brought close to or away from the intersection point "O" or the fixation target "A". In response to this, the computer 10 determines a range in which the subject "S" can sense the change region "M", whereby sensitivity of an eye is measured. At this stage, the subject "S" looking at the display screen 17 presses a button of an input mechanism of the input operation system 12 by hand operation, to notify the computer 10 that the subject "S" has sensed the change region "M". The computer 10 determines the sensible range of the change region on the basis of information of the change region "M" that is shown on the display screen 17 at the time of receiving a signal for notifying that the subject "S" has sensed the change region "M". The information of the change region "M" includes a distance of the change region to the intersection point "O" or the fixation target "A", and a degree of change of the image in the change region "M", for example, a degree of blurring in the case of using a blur.

The measurement system 1 determines the range that can be sensed by the subject "S", in response to hand operation for pressing the button of the input mechanism of the input operation system 12 by the subject "S", that is, in accordance with self notification from the subject "S". However, the determination can be performed based on information other than the self notification of the subject "S". A biological reaction tends to appear when the change region "M" is sensed. Thus, for example, the sensible range may be determined based on a change in biological signal by using a measuring device for measuring a biological signal of the subject "S", such as an electroencephalogram, a magnetoencephalogram, or blood flow information.

In this manner, the measurement system 1 shows the fixation target "A" on the display screen 17 to make the subject "S" focus on the fixation target "A", and in this state, continuously or intermittently brings the change region "M" close to or away from the intersection point "O" or the fixation target "A" while the line of sight is maintained. This enables quantitatively measuring sensitivity of an eye around a predetermined line of sight, with high accuracy.

In one embodiment, the change region "M" is preferably at least one continuous region that continuously extends from a side edge of the display screen 17 relative to the intersection point "O" or the fixation target "A", toward the intersection point "O" or the fixation target "A". The change region "M", which continuously extends from a side edge of the display screen 17, makes it possible to efficiently measure a sensible distance (shortest distance) in a right-left direction from the intersection point "O" or the fixation target "A" to the change region "M".

In one embodiment, the change region "M" is preferably at least one continuous region that continuously extends from an upper edge or a lower edge of the display screen 17 relative to the intersection point "O", toward the intersection point "O" or the fixation target "A". The change region "M", which continuously extends from an upper edge or a lower edge of the display screen 17, makes it possible to efficiently measure a sensible distance (shortest distance) in an up-down direction from the intersection point "O" or the fixation target "A" to the change region "M".

As shown in FIGS. 3A and 3B, the change region "M" may be at least one continuous region that continuously extends from an upper edge or a lower edge, and a side edge of the display screen 17 relative to the intersection point "O", toward the intersection point "O" or the fixation target "A". Particularly in this case, a sensible distance (shortest distance) in the up-down direction, the right-left direction, or a direction tilted from the right-left direction, from the intersection point O or the fixation target "A" to the change region "M", can be efficiently measured.

In one embodiment, the change region "M" is preferably formed on at least one of right and left sides bounded by a vertical line that is parallel to the up-down direction of the display screen 17 while passing the intersection point "O", and the change region "M" preferably does not cross the vertical line. As shown in FIGS. 3A and 3B, the change region "M" is formed so as to not cross a vertical line "L". This change region "M" corresponds to a side area of an eyeglass lens. Sensitivity for this change region "M" corresponds to sensitivity for the side area of an eyeglass lens and is thereby effectively used in designing the side area of an eyeglass lens.

Figure 4A:
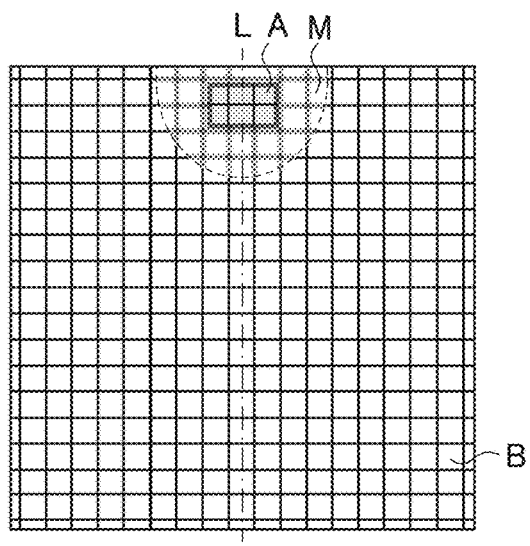
FIGS. 4A to 4C are explanatory drawings of other examples of the change regions used in one embodiment.
Figure 4B:
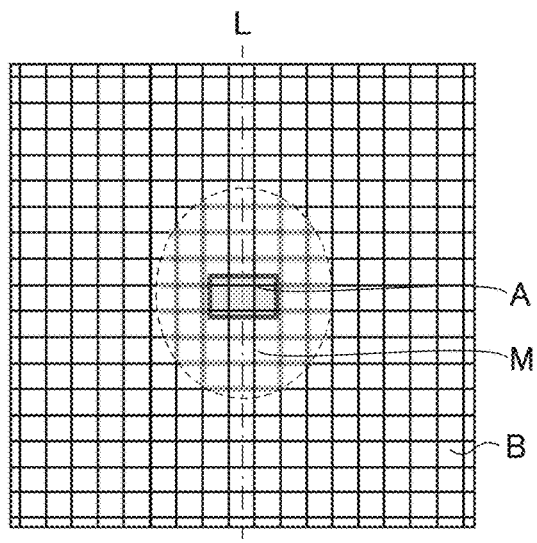
Figure 4C:
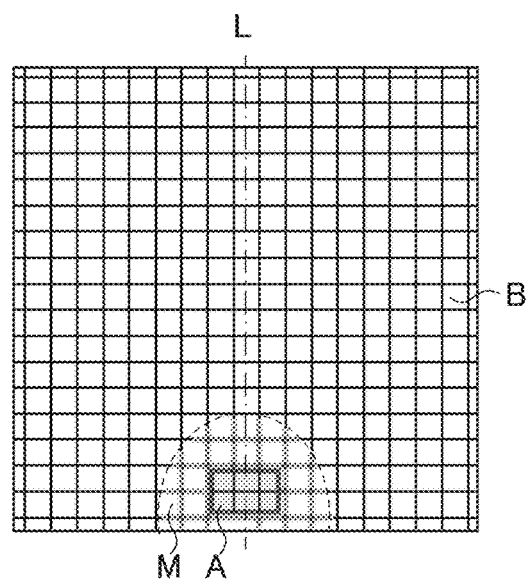

FIGS. 4A to 4C are explanatory drawings of examples of the change regions used in one embodiment. That is, in the one embodiment shown in FIGS. 4A to 4C, the fixation target "A" is a region having predetermined dimensions, and the change region "M" is provided so as to surround the region of the fixation target "A" and has a largest degree of change of the image of the pattern "P" in the display screen 17. In addition, an outer region "B" that surrounds the change region "M" is provided in the display screen 17, and the outer region "B" preferably has no change as in the region of the fixation target "A". It is also possible to measure sensitivity around a line of sight by using such a display. Under these conditions, the outer region "B" is not limited to a region having no change as in the region of the fixation target "A", and it may be a region having a small degree of change compared with that of the image in the change region "M".

In one embodiment, the change region "M" preferably includes a blurred image of the pattern "P". Blurring can occur in a side area of an eyeglass lens, in particular, a progressive power lens. Thus, it is preferable to measure sensitivity of an eye around a line of sight aimed at the fixation target "M", with respect to blurring in the side area, in terms of designing a lens suitable for sensitivity of the eye.

The head-mounted display 16 preferably shows the pattern "P" by changing the degree of blurring of the image of the pattern "P" in the change region "M" in a predetermined range, at the time of showing the change region "M" on the display screen 17. The sensible range in which an eye senses blurring around a line of sight varies depending on the degree of blurring and also on the person. Thus, it is preferable to show multiple images of the pattern "P" having mutually different degrees of blurring, on the display screen 17.

The sensitivity of an eye preferably includes information of a sensible distance of the change region "M" from the intersection point "O" in the condition in which the change region "M" can be sensed by the subject "S" and is most separated from the intersection point "O". The distance from the intersection point "O" is the shortest distance from the intersection point "0" to the change region "M". The information of the sensible distance relates to a distance from a line of sight, of a position where the change region "M" starts to be sensed. In view of this, the information of the sensible distance from the intersection point "O" in the condition in which the intersection point "O" is most separated, is preferably used as an index of sensitivity of an eye.

The sensible distance is determined in accordance with a degree of blurring in the change region "M". Thus, in one embodiment, information containing a set of the degree of blurring and the sensible distance corresponding to the degree of blurring is preferably used as an index of sensitivity of an eye. As the degree of blurring is lower, the sensible distance tends to be shorter. In consideration of this, it is preferable to design an astigmatism distribution in the side area in accordance with the information of the set of the degree of blurring and the sensible distance, so that a person wearing eyeglasses of progressive power lenses will not sense the degree of blurring in the side area.

Note that a line of sight that is aimed at the fixation target "A" is preferably in a direction different from that of a line of sight of the subject "S" looking forward straightly. This direction includes an up-down direction, a right-left direction, and a direction tilted from the right-left direction. In this manner, it is preferable to measure sensitivity for the change region around a line of sight aimed at any direction, in terms of designing an eyeglass lens suitable for sensitivity of an eye of each person.

In particular, a line of sight directed downward relative to a front line of sight corresponds to a line of sight when a person wearing eyeglasses looks at a near position by using near vision parts of progressive power lenses. Thus, in order to make it difficult for the person wearing eyeglasses to sense blurring of an image in a side area of the near vision part, it is preferable to measure sensitivity for the change region "M" around a line of sight directed downward relative to a front line of sight.

In one embodiment, in the pattern "P" shown on the display screen 17, the image of the pattern "P" in a region other than the change region "M" preferably has a constant degree of change irrespective of the position in the display screen 17. In the examples shown in FIGS. 4A to 4C, the degrees of blurring in the region of the fixation target "A" and in the outer region "B" are preferably the same. In a case in which the degree of change differs depending on the position (is uneven) in the region other than the change region "M", there is a possibility that a sensible range is not correctly determined. The degree of change in the region other than the change region "M" can be set as desired on the condition that it is constant. For example, in measuring sensitivity for blurring, the region other than the change region "M" preferably has a degree of blurring smaller than that in the change region "M", and more preferably has no blur.

The change region "M" may be shown on each of right and left sides of a line of sight at the same time, on the display screen 17, as shown in FIGS. 2, 3A, and 3B. However, the change region "M" may be shown on one side, and sensitivity relating to the change region "M" on a right side or a left side of a line of sight may be measured.

The measurement system 1 may collectively measure sensitivity of both eyes relating to the change region "M", but may measure it with respect to each eye.

Sensitivity of both eyes may be collectively measured by separately showing two patterns. One of the two patterns has the change region "M" in an area on an inner side (nose side) in the right-left direction of lines of sights of both eyes. The other has the change region "M" in an area on an outer side (side opposite to the nose side) in the right-left direction. In this case, sensitivities of both eyes on the outer side and on the inner side in the right-left direction are measured separately.

Sensitivity of one eye may be measured by separately showing two patterns. One of the two patterns has the change region "M" only in the area on the inner side (nose side) in the right-left direction. The other has the change region "M" only in the area on the outer side (side opposite to the nose side) in the right-left direction. Alternatively, sensitivity of one eye may be measured by showing a pattern having the change region "M" in an area on each side in the right-left direction. In these cases, sensitivities of one eye on the outer side and on the inner side are measured separately, or sensitivities of one eye on both sides in the right-left direction may be collectively measured at the same time.

Figure 5:
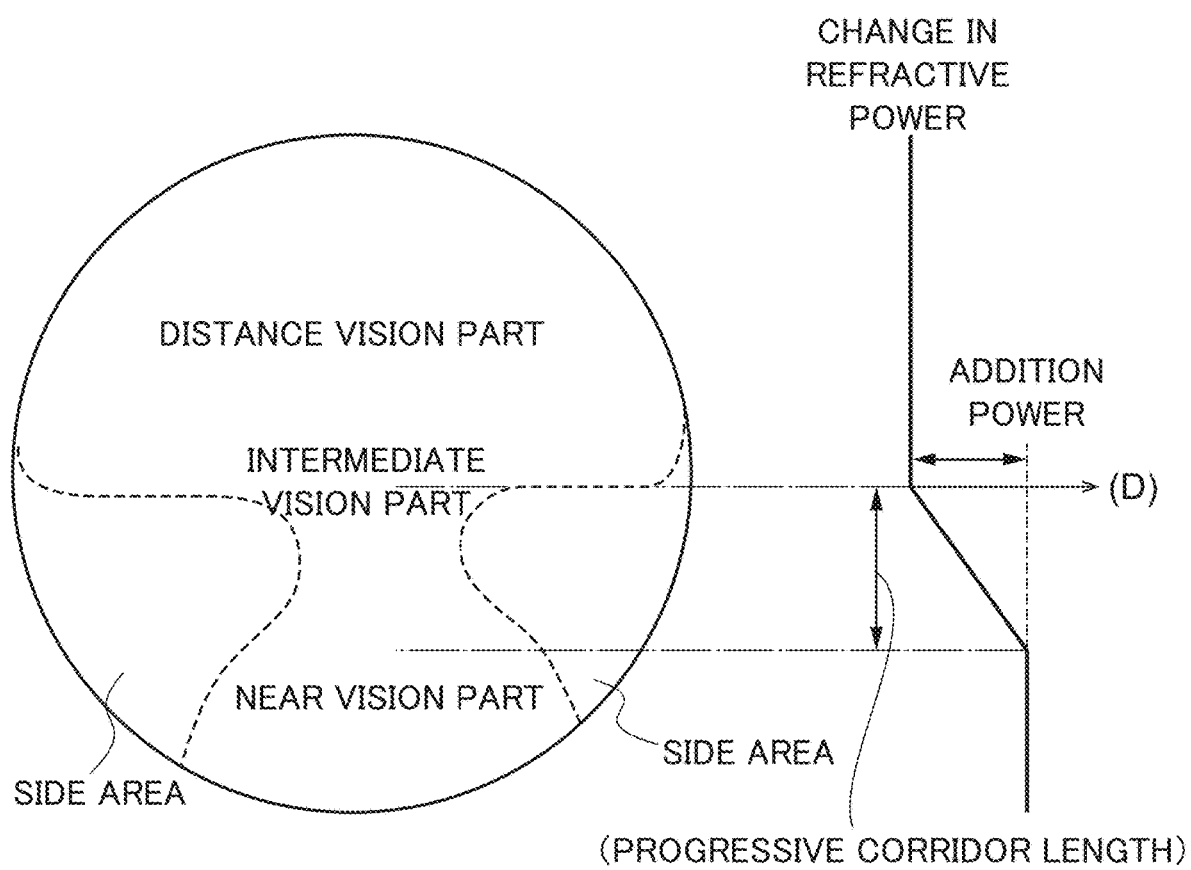
FIG. 5 schematically shows a progressive power lens.

Such a result of sensitivity can be effectively used in designing a progressive power lens among eyeglass lenses. FIG. 5 schematically shows a progressive power lens in a state of a circle-shaped lens substrate that is not edged to fit to the shape of an eyeglass frame.

As shown in FIG. 5, the progressive power lens is an eyeglass lens that has regions of a distance vision part for distance viewing, a near vision part for near viewing, and an intermediate vision part positioned between the distance vision part and the near vision part, and the progressive power lens changes in refractive power between the distance vision part and the near vision part.

In order to design a progressive power lens suitable for sensitivity of an eye of a person who will purchase eyeglasses, the purchaser is assumed as a subject "S" of the measurement system 1, and sensitivity of an eye of the subject "S" is measured.

This measurement provides information of sensitivity for the change region "M". On the basis of this information, a refractive power distribution in a progressive power lens is designed. In particular, side areas on right and left sides in the regions from the intermediate vision part to the near vision part often generate astigmatism to cause blurring or distorting of an image, whereby a purchaser tends to have uncomfortable wear feeling (uncomfortable feeling due to blurring or distorting of an image). In view of this, it is preferable to assume a purchaser as the subject "S", measure the sensitivity of an eye, and design a progressive power lens based on the measurement result so as to not give uncomfortable wear feeling.

For example, a distribution of astigmatism in a clear visual field area or a side area from the intermediate vision part to the near vision part is preferably adjusted in accordance with sensitivity of an eye for the change region "M". In one example in which sensitivity is low for a low degree of blurring, but is high for a high degree of blurring, a maximum astigmatism amount in the side area is reduced by dispersing regions having low astigmatism amounts, to a wide area.

As described above, the fixation target "A" is shown on the display screen 17 of the display device to make the subject "S" focus on the fixation target "A", and in this state, the change region "M" is continuously or intermittently brought close to or away from the intersection point "O" or the fixation target "A" while the line of sight is maintained. This enables quantitatively measuring sensitivity of an eye around a predetermined line of sight, with high accuracy. The sensitivity is an ability relating to whether the change region can be sensed, and therefore, it is possible to measure the range in which the change region "M" can be sensed, by continuously or intermittently bringing the change region "M" closer or farther away. The wear feeling of eyeglasses of a purchaser who will purchase eyeglasses differs depending on this sensitivity. Thus, an eyeglass lens suitable for a purchaser and not giving uncomfortable wear feeling can be provided.

In a case in which the subject "S" corrects the subject's eyes by using eyeglasses or the like, the measurement of sensitivity of an eye may be performed in the state in which the eyeglasses are worn. In this situation, it is preferable to obtain lens characteristics of the eyeglass lens of the eyeglasses that are worn and to correct the sensitivity. For example, information of the sensible distance is preferably corrected by using light ray tracking of an eyeglass lens. In addition, a degree of deformation in the change region "M", which is sensed by the subject "S", is preferably corrected in consideration of the shape of an eyeglass lens. In view of this, the sensitivity is preferably measured by preparing multiple eyeglass lenses having known lens characteristics in advance and using an eyeglass lens most appropriate for the subject "S" among these eyeglass lenses.

The measuring method for measuring sensitivity of an eye of a subject and a designing method for a progressive power lens of the present invention are detailed above. However, the present invention is not limited to the foregoing embodiments, and of course, various modifications and alterations may be made without departing from the gist of the present invention.

REFERENCE SIGNS LIST 1 measurement system
10 computer
12 input operation system
14 monitor
16 head-mounted display
17 display screen

The invention claimed is:
1. A measuring method for measuring sensitivity of an eye around a certain line of sight that is maintained by a subject, the measuring method comprising:

showing an image of a predetermined pattern on a display screen, the display screen being shown in front of an eyeball of the subject by a display device that is secured to a head of the subject;

showing a fixation target to be focused on by the subject, on the display screen, in order to make a line of sight of the subject be the certain line of sight;

showing a change region where the image of the predetermined pattern is changed, the change region being separated from an intersection point and the fixation target, the intersection point being where the certain line of sight of the subject focusing on the fixation target, crosses the display screen;

showing the change region where the image of the predetermined pattern is changed, on the display screen, in such a manner that the change region is continuously or intermittently brought close to or away from the intersection point or the fixation target in the display screen; and determining a range in which the subject can sense the change region, in response to the change region shown by bringing the change region close to or away from the intersection point or the fixation target, whereby the sensitivity of the eye is measured, wherein the fixation target is shown overlapping a part of the image of the pattern on the display screen, and the measuring method further comprises:

performing a first measurement by showing the fixation target at a first position on the display screen and determining a first range in which the subject can sense the change region; and performing a second measurement by showing the fixation target at a second position on the display screen, different from the first position, and determining a second range in which the subject can sense the change region.

2. The measuring method according to claim 1, wherein the change region is at least one continuous region that continuously extends from a side edge of the display screen relative to the intersection point, toward the intersection point or the fixation target.

3. The measuring method according to claim 2, wherein the change region is at least one continuous region that continuously extends from an upper edge or a lower edge of the display screen relative to the intersection point, toward the intersection point or the fixation target.

4. The measuring method according to claim 2, wherein the change region is formed on at least one of right and left sides bounded by a vertical line that is parallel to an up-down direction of the display screen while passing the intersection point, and the change region does not cross the vertical line.

5. The measuring method according to claim 2, wherein the fixation target is a predetermined region having predetermined dimensions, the change region is provided so as to surround the predetermined region of the fixation target and has a first degree of a change of the image of the pattern, the first degree of the change is a largest of all the change in the display screen, the change region is surrounded by a small-changed region or a no-changed region, the small-changed region having a second degree of the change, and the second degree of the change has a smaller degree of the change than the first degree of the change and the no-changed region has no degree of change.

6. The measuring method according to claim 2, wherein the change region includes a blurred image of the pattern.

7. The measuring method according to claim 2, wherein the sensitivity of the eye includes information of a sensible distance of the change region from the intersection point in the condition in which the change region can be sensed by the subject and is most separated from the intersection point.

8. The measuring method according to claim 1, wherein the change region is at least one continuous region that continuously extends from an upper edge or a lower edge of the display screen relative to the intersection point, toward the intersection point or the fixation target.

9. The measuring method according to claim 8, wherein the change region is formed on at least one of right and left sides bounded by a vertical line that is parallel to an up-down direction of the display screen while passing the intersection point, and the change region does not cross the vertical line.

10. The measuring method according to claim 8, wherein the fixation target is a predetermined region having predetermined dimensions, the change region is provided so as to surround the predetermined region of the fixation target and has a first degree of a change of the image of the pattern, the first degree of the change is a largest of all the changes in the display screen, the change region is surrounded by a small-changed region or a no-changed region, the small-changed region having a second degree of the change, and the second degree of the change has a smaller degree of the change than the first degree of the change and the no-changed region has no degree of change.

11. The measuring method according to claim 1, wherein the change region is formed on at least one of right and left sides bounded by a vertical line that is parallel to an up-down direction of the display screen while passing the intersection point, and the change region does not cross the vertical line.

12. The measuring method according to claim 1, wherein the fixation target is a predetermined region having predetermined dimensions, the change region is provided so as to surround the predetermined region of the fixation target and has a first degree of a change of the image of the pattern, the first degree of the change is a largest of all of the changes in the display screen, the change region is surrounded by a small-changed region or a no-changed region, the small-changed region having a second degree of the change, and the second degree of the change has a smaller degree of the change than the first degree of the change and the no-changed region has no degree of change.

13. The measuring method according to claim 1, wherein the change region includes a blurred image of the pattern.

14. The measuring method according to claim 13, further comprising showing the pattern by changing a degree of blurring of the image of the pattern in the change region in a predetermined range, at the time of showing the change region on the display screen.

15. The measuring method according to claim 1, wherein the sensitivity of the eye includes information of a sensible distance of the change region from the intersection point in the condition in which the change region can be sensed by the subject and is most separated from the intersection point.

16. The measuring method according to claim 15, wherein the sensible distance is determined in accordance with the degree of blurring, and the sensitivity of the eye includes information of a set of the degree of blurring and the sensible distance corresponding to the degree of blurring.

17. The measuring method according to claim 1, wherein the certain line of sight is a first line of sight, the first line of sight being made when the fixation target is shown at a first position on the display screen,
a second line of sight is made when the fixation target is shown at a second position on the display screen, the second line of sight being in a direction different from a direction of the first line of sight,
the first position on the display screen is located at a center of the display screen such that the first line of sight corresponds to the subject looking straight ahead, and
the method further includes showing the fixation target at the second position.

18. The measuring method according to claim 1, wherein the certain line of sight is directed downward relative to the line of sight of the subject looking forward straightly.

19. The measuring method according to claim 1, wherein the image of the pattern shown on the display screen, in a region other than the change region, has a constant degree of the change irrespective of the position in the display screen.

20. The measuring method according to claim 1, wherein the determining a range comprises determining a sensible distance of the change region from the intersection point, wherein the sensible distance is a separation distance at which the change region can be sensed by the subject when the change region is most separated from the intersection point.

21. A designing method for a progressive power lens suitable for an eye of a subject, the progressive power lens having regions of a distance vision part for distance viewing, a near vision part for near viewing, and an intermediate vision part positioned between the distance vision part and the near vision part, the progressive power lens changing in refractive power between the distance vision part and the near vision part, the designing method comprising:
showing an image of a predetermined pattern on a display screen, the display screen being shown in front of an eyeball of the subject by a display device that is secured to a head of the subject;
showing a fixation target to be focused on by the subject, on the display screen, in order to make a line of sight of the subject be a certain line of sight;
showing a change region where the image of the predetermined pattern is changed, the change region being separated from an intersection point and the fixation target, the intersection point being where the line of sight directed downward of the subject focusing on the fixation target, crosses the display screen;
showing the change region, where the image of the predetermined pattern is changed, on the display screen, in such a manner that the change region is continuously or intermittently brought close to or away from the intersection point or the fixation target in the display screen;
determining a range in which the subject can sense the change region, in response to the change region shown by bringing the change region close to or away from the intersection point or the fixation target, whereby the sensitivity of the eye is measured; and
designing a refractive power distribution suitable for the subject on a basis of information of the measured sensitivity of the eye, wherein
the fixation target is shown overlapping a part of the image of the pattern on the display screen,
the certain line of sight is a first line of sight, the first line of sight being made when the fixation target is shown at a first position on the display screen,
a second line of sight is made when the fixation target is shown at a second position on the display screen, the second line of sight being in a direction different from a direction of the first line of sight,
the first position on the display screen is located at a center of the display screen such that the first line of sight corresponds to the subject looking straight ahead,
the method further includes showing the fixation target at the second position, and
the method further comprises:
performing a first measurement by showing the fixation target at a first position on the display screen and determining a first range in which the subject can sense the change region; and
performing a second measurement by showing the fixation target at a second position on the display screen, different from the first position, and determining a second range in which the subject can sense the change region.

* * * * *